United States Patent [19]
Littleford

[11] Patent Number: 4,552,157
[45] Date of Patent: Nov. 12, 1985

[54] OPEN CURVE, ATRIAL "J" ELECTRODE

[76] Inventor: Philip O. Littleford, 2400 Bedford Rd., Orlando, Fla. 32803

[21] Appl. No.: 389,170

[22] Filed: Jun. 17, 1982

Related U.S. Application Data

[63] Continuation-in-part of Ser. No. 168,742, Jul. 14, 1980, Pat. No. 4,357,947, and Ser. No. 231,103, Feb. 3, 1981, Pat. No. 4,401,127.

[51] Int. Cl.⁴ .............................................. A61N 1/04
[52] U.S. Cl. .................................. 128/786; 128/419 P
[58] Field of Search ................................ 128/784–786, 128/419 P, 642

[56]  References Cited
U.S. PATENT DOCUMENTS

| | | | |
|---|---|---|---|
| 4,401,127 | 8/1983 | Littleford | 128/786 |
| 4,422,460 | 12/1983 | Pohndorf | 128/786 |

OTHER PUBLICATIONS

Littleford et al., "A New Temporary Atrial Pacing ... " PACE, vol. 4, Jul.-Aug. 1981, pp. 458–464.

*Primary Examiner*—Lee S. Cohen
*Attorney, Agent, or Firm*—Duckworth, Allen, Dyer & Pettis

[57] ABSTRACT

A flexible electrode catheter for rapid endocardial insertion has a "J"-shaped curved configuration. A wing extends laterally from the catheter at the proximal end, and has an established relationship between the lateral direction of the wing and the direction of the curve, allowing the physician to control the orientation of the distal end during and after insertion within the heart. The wing may then be used to stabilize the electrode by taping to the patient's skin. The curved end is opened between 20°–50° from the longitudinal axis of the catheter.

4 Claims, 7 Drawing Figures

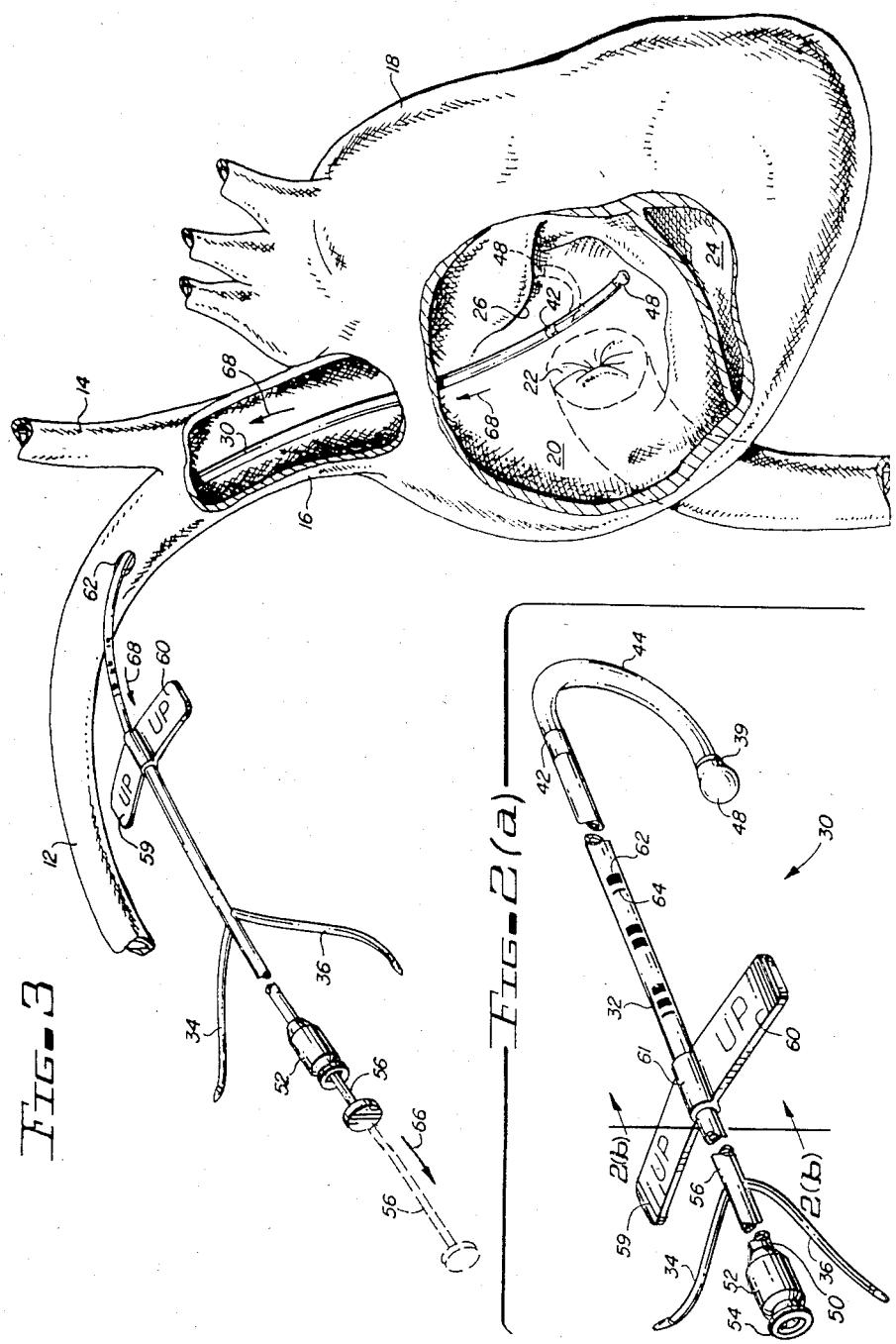

OPEN CURVE, ATRIAL "J" ELECTRODE

This application is a continuation-in-part of the following applications: Ser. No. 168,742, filed July 14, 1980, now U.S. Pat. No. 4,357,947; and Ser. No. 231,103, filed Feb. 3, 1981, now U.S. Pat. No. 4,401,127.

The present invention relates generally to medical and surgical devices and methods, and in particular, relates to electrode catheters which are designed to be inserted through the circulatory system and into the heart for purposes of permitting an artificial electronic stimuli to pace the heart.

The term "pacemaker" generally applies to devices in a family of products which are electrically connected through an electrode for providing electronic pacing impulses to a patient's heart.

One type of pacemaker, referred to as a permanent pacemaker, is packaged in a small, portable container and is usually implanted under the patient's skin in a major surgical technique. Pacemaker implants are carried out in an operating room or similar facility equipped with a fluoroscope, which permits the attending physician to precisely position the extremity of the permanent pacemaker electrode in a desired location in the heart.

Another type of pacemaker provides temporary pacing stimuli to the patient, and employs an electrode which is designed to be inserted by a physician in a rigid manner while the patient is in an emergency room, intensive care unit, catheter laboratory or similar facility.

Generally, a fluoroscopic unit is used during insertion of a temporary pacing electrode, but occasionally in emergency situations, "blind insertion" has been attempted, but with limited success.

It is well known that the heart may be effectively "paced" by an electronic stimulus located within the right atrium. However, it is very difficult to locate the extremity of an electrode in an appropriate location which is stable in the right atrium, even with the benefit of fluoroscopy. Without the benefit of fluoroscopy (as during the blind insertion of a temporary pacing electrode under the emergency circumstances described above), it has been heretofore unknown to insert a temporary pacing electrode in the right atrium. Because of the inability to effectively locate an electrode within the atrium in a stable manner, most pacing electrodes (both temporary and permanent) are inserted in the right ventricle, which offers stable positioning. However, it is also difficult to manipulate a pacing electrode through the tricuspid valve into the right ventricle for ventricular pacing without fluoroscopy.

In U.S. Pat. No. 4,166,469, issued Sept. 4, 1979, there is disclosed apparatus and a related method for the rapid and atraumatic insertion of pacemaker electrodes through the subclavian vein.

SUMMARY OF THE INVENTION

The present invention contemplates apparatus for rapidly and accurately inserting a pacing electrode, particularly a temporary pacing electrode, into the right heart and thereafter stabilizing the electrode. The invention is also based, in part, on the recognition that the insertion through the right subclavian vein of a curved, or "J" electrode into the right atrium will always engage the right atrium in a stable manner when the electrode is oriented and manipulated in a predetermined direction and manner.

More particularly, the present invention is directed to a pacing electrode including a flexible conductor having an outer, electrically insulating sheath about the conductor, the conductor and the sheath forming a "J"-shaped curve or bend at the distal end with the conductor having an electrical terminal along the distal end, the terminal adapted for making electrical endocardial contact. Means are further provided along the sheath for indicating the orientation of the curve after the distal end has been inserted into the heart, and for stabilizing the electrode after electrical contact has been properly established between the terminal and the heart.

In a preferred embodiment of the electrode in accordance with the present invention, the orienting and stabilizing means is dimensioned along the sheath at a position outside the patient's body when the distal end has been inserted into the heart. Suitably, the orienting and stabilizing means comprises a wing extending laterally from the sheath, the lateral direction of the wing indicating the orientation of the curve at the distal end. One side of the wing is provided with means for indicating which side of the wing should be facing away from the patient. The desired orientation will be obtained in accordance with the present invention when the wing lies flat against the patient's skin, with the "UP" indicating means properly positioned. In the case of an atrial electrode, the distal end forms a "J" shaped flexible curve. To compensate for those patients having an enlarged right atrium secondary to chronic heart failure, it has been found that opening the plane of the "J"-shaped arteriorally away from the plane of the wings and about the longitudinal axis of the catheter permit a more anterior lateral orientation of the electrode end in vivo. Suitably, the angle of opening is between 20°-50°, and is preferably on the order of 30°.

DESCRIPTION OF THE DRAWINGS

FIG. 2(a) is a front perspective view, partially cut away, illustrating an electrode in accordance with the present invention.

FIG. 3 is a front view of the human heart, the subclavian and cephalic veins and their connection to the superior vena cava, with portions of the superior vena cava and the heart cut away to illustrate the manner in which an atrial electrode in accordance with the present invention is utilized.

DETAILED DESCRIPTION OF THE PREFERRED EMBODIMENT

A preferred embodiment of an atrial electrode in keeping with the present invention will now be described with reference to FIGS. 1-3. While one particular structural arrangement of a bipolar temporary electrode in accordance with the present invention is shown and described, it will be understood by those skilled in the art from the detailed description set forth below that the design may be adapted for unipolar electrodes as well as permanent electrodes, and that various modifications may be made in the design without departing from the spirit and scope of the present invention.

Figure 1A:
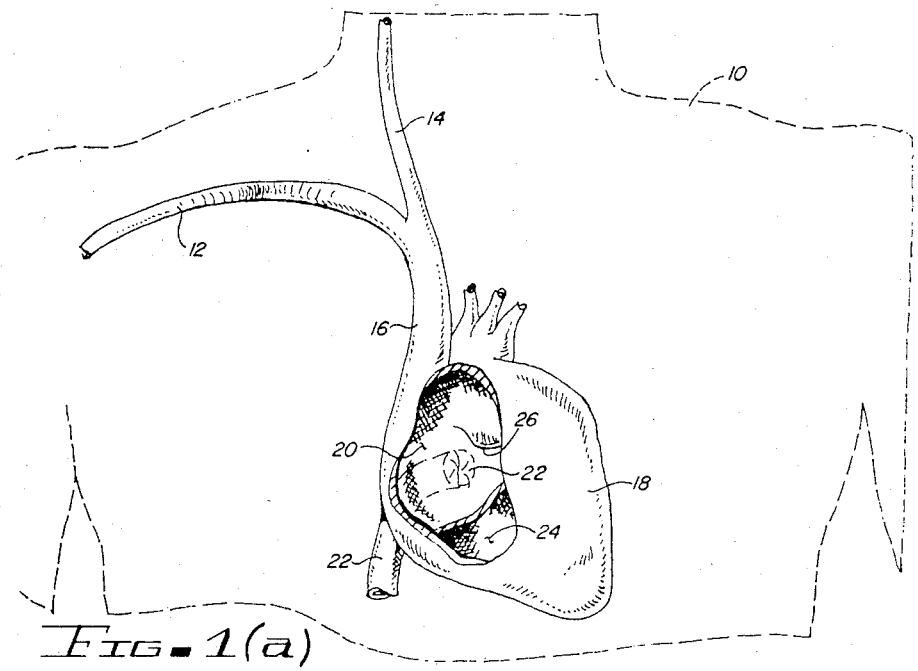
FIG. 1(a) is a front view of a portion of the human anatomy, particularly illustrating the human heart with a portion cut away to show the inside of the right atrium and a portion of the right ventricle.
Figure 1B:
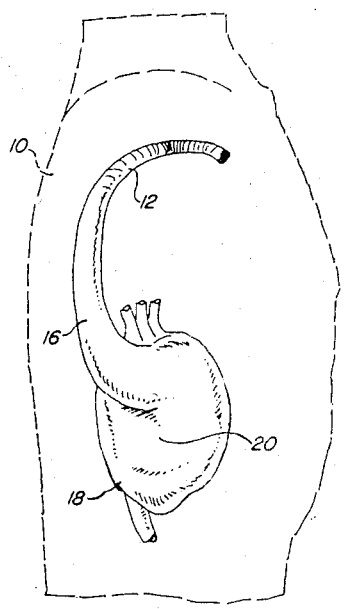
FIG. 1(b) is a side view illustrating a portion of the human anatomy, and specifically illustrating the curvature of the subclavian vein as it enters and connects with the superior vena cava.

With particular reference to FIGS. 1(a) and (b), there is illustrated a human body 10, the right subclavian vien 12, the cephalic vein 14 and the superior vena cava 16. The drawing of FIG. 1 is fanciful in nature, it being understood that the drawing is not to scale, but serves only to illustrate the functional relationships of the heart and the associated circulatory system.

Element 18 refers to the heart, including the right atrium 20, the right ventricle 24, and the inferior vena cava 22. The wall between the right atrium 20 and the right ventricle 24 is cut away in the area where the tricuspid valve would normally be located for purposes of permitting illustration of the right ventricle. As is known, blood from the arms, head and body flow into the right atrium 20 via the superior vena cava 16 from, among others, the subclavian and cephalic veins 12 and 14. Blood from the trunk and legs enters the right atrium 20 via the inferior vena cava 22.

As is also known, there is a portion of the right atrium known as the right atrial appendage, identified as element 26 in FIG. 1(a). The right atrial appendage 26 is a small earlike appendage forming a pocket located anteriorly and superiorly on the right atrial wall, the inner surface of which is particularly susceptible to pacing.

Figure 2B:
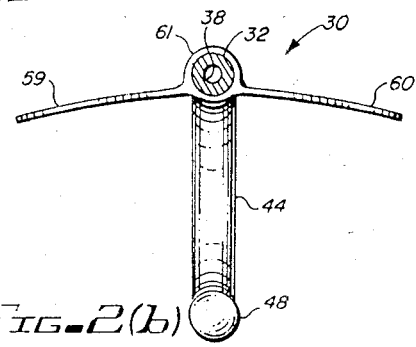
FIG. 2(b) is a front sectional view of the electrode of FIG. 2(a), along the line 2(b)-2(b).
Figure 2C:
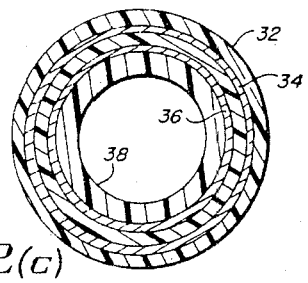
FIG. 2(c) is an enlarged illustration of the end section of the view of FIG. 2(b).

Noting FIG. 2(b), it is seen that the curvature of the subclavian vein to the connection with the superior vena cava 16 is not flat, as it appears in FIG. 1(a), but rather is curved toward the rear of the patient's body, i.e. in the direction toward the spinal column, coming from the forward surface of the body 10.

Reference is now made to FIGS. 2(a), (b) and (c), which disclose a temporary atrial electrode in accordance with the present invention.

The electrode, referred to generally by the reference numeral 30, includes a flexible, electrically insulating sheath 32 with a pair of concentric conductors 34, 36 surrounding a central lumen 38 which may extend through the electrode 30 to the distal end 39. Each of the conductors 34, 36 are insulated by a layer of insulating material (not numbered—see FIG. 2(c)). If the insulating material of the sheath 32 has sufficient flexibility and a good elastic memory, the central lumen 38 may be eliminated.

Each of the conductors 34, 36 are exposed at the surface of the outer insulating sheath 32, in order to permit electrical contact in the heart when the electrode 30 is in place. By way of example, conductor 34 may have a surface terminal 42 and inner concentric conductor 36 may have a surface terminal 48 at the distal extremity 39. Typically, the outer conductor 34 will serve to shield the inner conductor 36, and the inner conductor will therefore be relied upon to provide pacing signals at the distal extremity 39 of the electrode 30. In accordance with a preferred embodiment of the present invention, the terminal 48 consists of a spherical conductor connected electrically with the inner conductor 36.

Referring again to FIG. 2(a), the proximal extremity 50 of the electrode 30 includes a hub 52 having an opening 54 which communicates with the central lumen 38. Each of the concentric conductors 34, 36 include external portions which likewise exit the electrode 30 at the proximal end 50, typically in the manner shown in FIG. 2(a). As is well known, the proximal extremities of each conductor 34, 36 may be connected to a temporary pacemaker (not shown).

As is shown on the right-hand side of FIG. 2(a), the electrode 30 is provided with a somewhat gentle curve 44 between the terminal 42 and the distal extremity 39 which permits the conductor terminal 48 at the distal extremity 39 to be pointed in a direction approximately 180° from the direction of the electrode 30, and in a plane substantially parallel with the plane of the electrode; that is to say, when the main body of the electrode 30 is lying on a flat surface, the curved portion 44 and the distal extremity 39 are likewise lying in the plane of the same flat surface (see FIG. 2(b)). The insulating sheath 32, including the insulative materials between the conductive electrodes 34, 36 are of a material which has an elastic memory so that when the curved portion of the distal extremity 39 of the electrode 30 is straightened, the curved portion at the distal extremity 39 will thereafter resume its curved configuration. A number of conventional silastic and other non-toxic plastic materials are suitable for this purpose.

Straightening of the curve 44 of the electrode 30 during insertion may be accomplished by simple manipulation with the hands, or with a stylet 56 having an outer diameter sufficiently small to permit it to pass through the opening 54, down the central lumen 38 to straighten the curved end and hold straight the entire electrode, including the distal extemity 39. The stylet 56 must be sufficiently flexible to permit the electrode to pass through the subclavian vein 12, the superior vena cava 16 and into the right atrium 20.

In accordance with the present invention, the electrode 30 is provided with means for indicating the relative position of the curved distal extremity 39 with respect to the axial direction of the electrode 30 and the plane in which the electrode and the curved extremity lies. In the embodiment shown in FIG. 2(a), the indicating means in this regard comprises a pair of flat, relatively flexible plastic wings 59, 60 which are joined by a sleeve 61 to the proximal extremity and extend laterally from the outer insulating sheath 32. As is shown in FIG. 2(a), the indicating wings 59 and 60 extend generally perpendicular to the plane of the curve 44, the distal extremity 39 and the main body of the electrode 30. As shown in FIGS. 2(a) and (b), the wings 59, 60 are curved slightly downward and include the notation "UP" on the upper side intended to be away from the patient's body, as described further below.

The electrode 30 further includes means for indicating the distance along the insulating sheath 32 from the curve in the distal extremity 39. In the embodiment of FIG. 2(a), this distance indicating means comprises a series of gradations along the insulating sheath 32 forward of the indicating wings 59, 60 in the direction of the curve of the extremity 39. Typically, the gradations may include wide gradations 62 and thin gradations 64, each wide gradation indicating 10 cm. segment and each thin gradation indicating a 5 cm. segment; thus, an individual marking of two wide gradations and one thin gradation would indicate a 25 cm. distance from the curved end.

The method in which the electrode of the present invention is employed for insertion through the right subclavian vein and into the right atrium without the use of fluoroscopy will now be described with reference to FIG. 3.

Before beginning the technique of inserting the electrode 30 in the manner hereinafter described, the patient is properly prepared and normal sterilization techniques are observed.

Initially, a puncture is made through the patient's skin in the area adjacent the clavicle so as to pass a small, thin-walled 18 gauge needle into the right subclavian vein 12, to thereafter permit the introduction of a removable introducer in the manner which is clearly described in U.S. Pat. No. 4,166,469. The technique for inserting a removable introducer sleeve into the right subclavian vein is clearly described in the specification of the patent, and is incorporated here by reference.

Once that sleeve is properly inserted, the curve 44 of the electrode 30 is straightened. The electrode 30 is then inserted down a removable introducer sleeve (not shown in FIG. 3, but see sleeve 56 in FIG. 11 of the aforementioned U.S. Pat. No. 4,166,469). Once the straightened distal extremity 39 of the electrode is inserted down the introducer sleeve into the subclavian vein 12, it is then manipulated through the superior vena cava 16 and into the right atrium 20. The removable introducer sleeve is then removed by peeling it away, allowing the wings 59, 60 to be positioned close to the entrance site into the subclavian vein 12.

At this point in the technique, the electrode 30 has been inserted as desired so that the straightened distal extremity 39 is positioned in the right atrium 20. It will be understood that the insertion technique thus far described leaves the indicating wings 59 and 60 exteriorly of the patient's skin. As a next step, the attending physician ensures that the indicating wings 59 and 60 are lying substantially parallel to the plane of the patient's skin, and with the words "UP" facing the physician. If a style is being used, the stylet is removed. In either event, the curve 44 will resume its normal, curved configuration, as is shown by dotted lines on the right side of FIG. 3, as the curved end passes into the right atrium.

If the physician has inserted the electrode a sufficient distance into the subclavian vein 12 (and down the superior vena cava 16 and into the right atrium 20), as is determined by reference to the indicating marks 62, 64 along the outer sheath 32, and if the indicating wings 59 and 60 are positioned in the manner described above, then the curved distal extremity 39 will assume a direction in which the terminal electrode 48 is pointed directly upward toward the right atrial appendage 26. This is because of the unique relationship of the curvature from the right subclavian vein 12, running down the superior vena cava 16 and into the right atrium 20, as is clearly shown in FIG. 1(b). As was noted previously, the subclavian vein 12 actually curves slightly backward toward the spinal column as it communicates with the superior vena cava 16, the superior vena cave communicating with the right atrium 20 at the rear of the heart 18. Thus, the indicating wings 59 and 60 and the curvature of the curve 44 are oriented such that when the indicating wings 59 and 60 are positioned substantially parallel to the patient's skin and with the "UP" side facing the physician, then the curve 44 at the distal extremity 39 is formed so that the conductive terminal 48 is pointed in the desired manner in the pocket under the right atrial appendage 26.

Next, the attending physican connects the conductors 34, 36 to the pacemaker pulse generator and then pulls the electrode 30 slightly outward away from the puncture wound in the skin and away from the subclavian vein 12, as is shown by the arrows 68 in FIG. 3. The electrode 30 may be withdrawn in this manner a distance of between 1 to 7 centimeters, as determined by reference to the gradations 62, 64 so as to ensure that the conductive terminal 48 engages the surface underneath the right atrial appendage 26. Typically, the physician will ascertain appropriate electrode "capture" by referring to the pulse generator. Because of the spherical configuration of the terminal 48, that terminal makes a broad electrical contact with the wall of the right atrium 20 in the pocket of the appendage 26, but without damage to the wall. The terminal 48 stays in the desired location because of the tension at the curve 44, despite continual movement of the atrial wall.

It will be appreciated that the manipulative steps described above can take place without the benefit of fluoroscopy, thus permitting a temporary electrode to be placed easily and quickly into the right atrium 20 for purposes of obtaining the benfits of physiological atrail pacing under emergency or temporary conditions.

An alternative embodiment of the winged atrail electrode previously described will now be described with reference to FIG. 4. This alternative embodiment is designed to provide a universally adaptable atrial electrode which may be inserted through the right subclavian vein for all patients, including those patients having an enlarged right atrium secondary to chronic heart failure.

Figure 4:
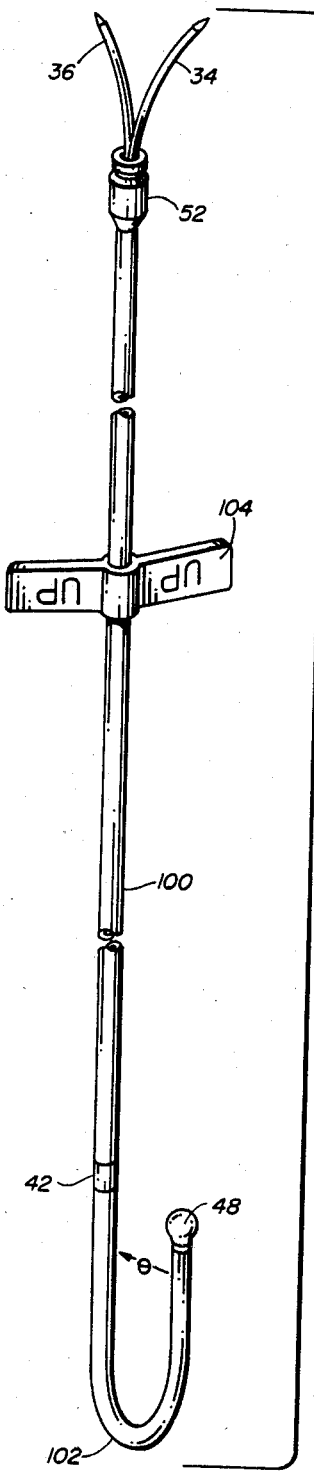
FIG. 4 is a top plan view of an alternative embodiment of an atrial electrode catheter in accordance with the present invention.

In order to solve these difficulties, the alternative embodiment of the atrail electrode, referred to generally as 100 in FIG. 4, is provided with an open curve at the insertion extremity, which curve 102 is rotated by an angle Theta ($\theta$), which is between 20° and 50°, and preferably about 30°, from a plane which passes through the longitudinal axis of the remainder of the electrode 100, and which plane is normal to the wings 104. This angular relationship is shown in FIG. 4. In this alternative embodiment, the opening of the curve away from the plane of the longitudinal axis just described permits a compensation for any of patient difficulties noted earlier.

I claim:

1. A pacing electrode for insertion through a puncture wound and through the circulatory system into a patient's heart, said electrode comprising
    (a) a flexible conductor having an outer insulating sheath, said sheath and conductor including an oblong body portion, a distal portion and a proximal end, said distal portion extending in a direction away from the axial direction of said body portion, said distal portion having sufficient flexibility and elastic memory so as to be straightened for passage through the patient's circulatory system and for reforming the extension in said direction after passage into the patient's heart;
    (b) a conductive terminal at the end of said distal portion of said conductor for electrical connection within the heart;
    (c) means along said body portion at said proximal end of said conductor for indicating said direction of said distal portion;

(d) means adjacent said proximal end of said sheath for interconnection to a pacemaker pulse generator, said indicating means including a wing joined to said sheath adjacent said proximal end, said wind extending away from said conductor in a fixed relation to the direction of said distal portion;

(e) said distal portion of said conductor is inserted into the heart with the proximal end and said indicating means extending outside of said puncture wound, whereby said distal portion may be located in a desired position by manipulation of said proximal end with reference to said indicating means; and wherein (f) the plane of said distal portion is rotated between 20° and 50° away from a plane which is normal to the direction of said wings.

2. The pacing electrode recited in claim 1 wherein said angle of rotation is approximately 30°.

3. A pacing electrode for insertion through a puncture wound in a patient's body and through the circulatory system including the superior vena cava and into the right atrium of the patient's heart, said electrode comprising:

(a) a flexible conductor having an outer insulating sheath, said conductor and sheath including an oblong body portion, a distal portion and a proximal end, said distal portion extending in a direction away from the axial direction of said body portion, said distal portion having sufficient flexibility and elastic memory so as to be straightened for passage through the patient's circulatory system and for reforming the extension in said direction of said distal portion after passage into the patient's heart;

(b) a conductive terminal at the end of said distal portion of said conductor for electrical interconnection within the heart;

(c) a wing joined to said body portion adjacent said proximal end of said conductor, the direction of said wing having a fixed relation with the direction of said distal portion, such that the plane of said distal portion is rotated between 20° and 50° away from a plane which is normal to the direction of said swing; and (d) means adjacent said proximal end of said sheath for interconnection to a pacemaker pulse generator.

4. A pacing electrode for rapid endocardial insertion into a patient's body comprising:

(a) a flexible conductor including a conductor and having an outer, electrically insulating sheath about said conductor, said conductor and said sheath forming a flexible curve at one end with said conductor having an exposed terminal along said flexible curved end, said terminal adapted for making electrical endocardial contact;

(b) means along said sheath and extending therefrom for stabilizing said electrode against the patient's skin after insertion; and wherein (c) said curve is rotated at an angle between about 20° and 50° from a plane passing through the longitudinal axis of the uncurved remainder of said electrode and normal to said stablizing means.

* * * * *